(12) United States Patent
Whipple et al.

(10) Patent No.: US 6,214,023 B1
(45) Date of Patent: Apr. 10, 2001

(54) ULTRASONIC SURGICAL INSTRUMENT WITH REMOVABLE CLAMP ARM

(75) Inventors: Gary Whipple, South Attleboro, MA (US); David L. Hunt; Richard F. Schwemberger, both of Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/337,077

(22) Filed: Jun. 21, 1999

(51) Int. Cl.[7] .................................................. A61B 17/32
(52) U.S. Cl. ............................................. 606/169; 604/22
(58) Field of Search ................................... 606/169, 170, 606/171–180; 604/22

(56) References Cited

U.S. PATENT DOCUMENTS

| 4,122,856 | 10/1978 | Mosior et al. ................... 128/311 |
| 5,322,055 | 6/1994 | Davison et al. ................... 601/2 |
| 5,591,182 | 1/1997 | Johnson ........................... 606/151 |
| 5,676,678 | 10/1997 | Schad ................................ 606/170 |
| 5,810,879 | 9/1998 | De Guillebon ................... 606/205 |
| 5,873,873 | 2/1999 | Smith et al. ...................... 606/1 |
| 5,980,510 | * 11/1999 | Tsonton et al. ................... 606/1 |
| 6,036,667 | * 3/2000 | Manna et al. ..................... 604/22 |

FOREIGN PATENT DOCUMENTS

| 19534618 A1 | 3/1997 | (DE) . |
| WO 98/14126 | 4/1998 | (WO) . |
| WO98/34543 | 8/1998 | (WO) . |

OTHER PUBLICATIONS

Japan Appln. No. 7–81469, dated 6 Apr. 199f; Applicant Olympus Optical Co., Ltd.
Japan Publication No. HEI 8–275949, dated Oct. 22, 1996; Applicant Olympus Optical Co., Ltd.
Japan Appln. No. 1–145053, dated Jun. 7, 19891; Applicant Olympus Optical Co., Ltd.
Japan Publication No. HEI 8–275952, dated Oct. 22, 1996; Applicant Olympus Optical Co., Ltd.

* cited by examiner

Primary Examiner—Henry J. Recla
Assistant Examiner—Lien Ngo
(74) Attorney, Agent, or Firm—Verne E. Kreger, Jr.

(57) ABSTRACT

The present invention describes ultrasonic surgical instruments that include a mechanism for clamping tissue against an ultrasonic blade, including an arrangement for detachably mounting a clamp arm to the instrument. The ultrasonic surgical instrument comprises a waveguide adapted to be acoustically coupled to an ultrasonic transducer, and to transmit ultrasonic energy to an end-effector located at the distal end of the waveguide. A support tube extends from a handle assembly and surrounds at least a portion of the waveguide, terminating proximal to the end-effector. A clamp arm is detachably mounted to the distal end of the support tube. An actuation element is operatively coupled to the clamp arm. The ultrasonic surgical instrument may also include a clamp arm release. The actuation element comprises a first range of motion and a second range of motion, whereby moving the clamp arm release from a second position to a first position increases allowable motion of the actuation element from the second range of motion to the first range of motion, thereby facilitating release of the clamp arm from the support tube. The ultrasonic surgical instrument may include the capability for the clamp arm, actuation element, support tube and waveguide to rotate within the handle assembly.

21 Claims, 9 Drawing Sheets

ULTRASONIC SURGICAL INSTRUMENT WITH REMOVABLE CLAMP ARM

This application is related to the following patent applications; application Ser. No. 08/949,050 filed Oct. 10, 1997, now U.S. Pat. No. 5,980,510; application Ser. No. 08/770,550 filed Dec. 23, 1996, now U.S. Pat. No. 6,051,010; and application Ser. No. 08/949,049 filed Oct. 10, 1997, which are hereby incorporated herein by reference.

FIELD OF THE INVENTION

The present invention relates generally to ultrasonic surgical instruments that include a mechanism for clamping tissue against an ultrasonic blade, and more particularly to an ultrasonic surgical instrument including an arrangement for detachably mounting a clamp arm to the ultrasonic surgical instrument

BACKGROUND OF THE INVENTION

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, may be used to cut, dissect, or cauterize tissue. Ultrasonic instruments utilizing solid core technology are particularly advantageous because of the amount of ultrasonic energy which may be transmitted from the ultrasonic transducer through the waveguide to the surgical end-effector. Such instruments are particularly suited for use in minimally invasive procedures, such as endoscopic or laparoscopic procedures, wherein the end-effector is passed through a trocar to reach the surgical site.

Solid core ultrasonic instruments adapted for use in surgery and, more particularly, for use in minimally invasive surgery, are well known in the art. For example, U.S. Pat. No. 5,322,055, and International publication number WO 98/14126 illustrate clamp coagulator surgical instruments which utilize solid core ultrasonic technology. Clamp coagulators such as those illustrated utilize clamp arms to apply pressure to tissue, forcing contact between tissue and the distal end of the ultrasonic waveguide which is generally referred to as the blade.

The clamp arm of clamp coagulator instruments such as those described in U.S. Pat. No. 5,322,055 generally include a pad, often made from a polymer, to limit contact between the active ultrasonic waveguide and the clamp arm. In such instruments, the clamp pad may become worn or contaminated during use in surgical procedures, requiring the entire instrument to be discarded. Thus, it would be advantageous to provide a simple and cost effective way to replace worn or contaminated clamp pads. It would also be advantageous to provide a means for attaching sterile clamp pads during surgical procedures. It would further be advantageous to provide ultrasonic clamp coagulating instruments with removeable and replaceable clamp arms and clamp arm/pad combinations. It would also be advantageous to provide ultrasonic clamp coagulators particularly adapted to allow simple removal and replacement of clamp arms.

SUMMARY OF THE INVENTION

Described is an ultrasonic surgical device comprising a transducer adapted to convert electrical energy into mechanical motion, attachable to an ultrasonic surgical instrument including a handle assembly adapted to receive the transducer. The ultrasonic surgical instrument comprises a waveguide adapted to be acoustically coupled to the transducer, and to transmit ultrasonic energy to an end-effector located at the distal end of the waveguide. A support tube extends from the handle assembly and surrounds at least a portion of the waveguide, terminating proximal to the end-effector. A clamp arm is detachably mounted to the distal end of the support tube. An actuation element is operatively coupled to the clamp arm.

The ultrasonic surgical instrument may include the capability for the clamp arm, actuation element, support tube and waveguide to rotate within the handle assembly. The ultrasonic surgical instrument may also include a clamp arm release. The actuation element comprises a first range of motion and a second range of motion, whereby moving the clamp arm release from a second position to a first position increases allowable motion of the actuation element from the second range of motion to the first range of motion, thereby facilitating release of the clamp arm from the support tube.

In another embodiment of the present invention, an ultrasonic surgical instrument comprising a handle assembly, a waveguide, an end-effector located at the distal end of the waveguide, and a support tube extending from the handle assembly and surrounding at least a portion of the waveguide, with the support tube separable into at least two portions. The clamp arm may be mounted to a distal portion of the separable support tube, and an actuation element, also separable into at least two portions, is operatively coupled to the clamp arm.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

The present invention is particularly directed to an improved ultrasonic surgical instrument configured tissue cutting, coagulation, and/or clamping during surgical procedures. The present instrument can readily be configured for use in both open surgical procedures, as well as laparoscopic or endoscopic procedures. Versatility is facilitated by selective use of ultrasonic energy. When ultrasonic components of the instrument are inactive, tissue can be readily gripped and manipulated, as desired, without tissue cutting or damage. When the ultrasonic components are activated, the instrument permits tissue to be gripped for coupling ultrasonic energy into the tissue for coagulation, with application of increased pressure facilitating tissue cutting and coagulation. If desired, ultrasonic energy can be applied to tissue without use of the clamping mechanism of the instrument by appropriate manipulation of the ultrasonic end-effector.

As will become apparent from the following description, it is contemplated that an instrument according to the present invention will be used in association with an ultrasonic transducer of a surgical system, whereby ultrasonic energy from the transducer provides the desired ultrasonic activation of the instrument.

Figure 1:
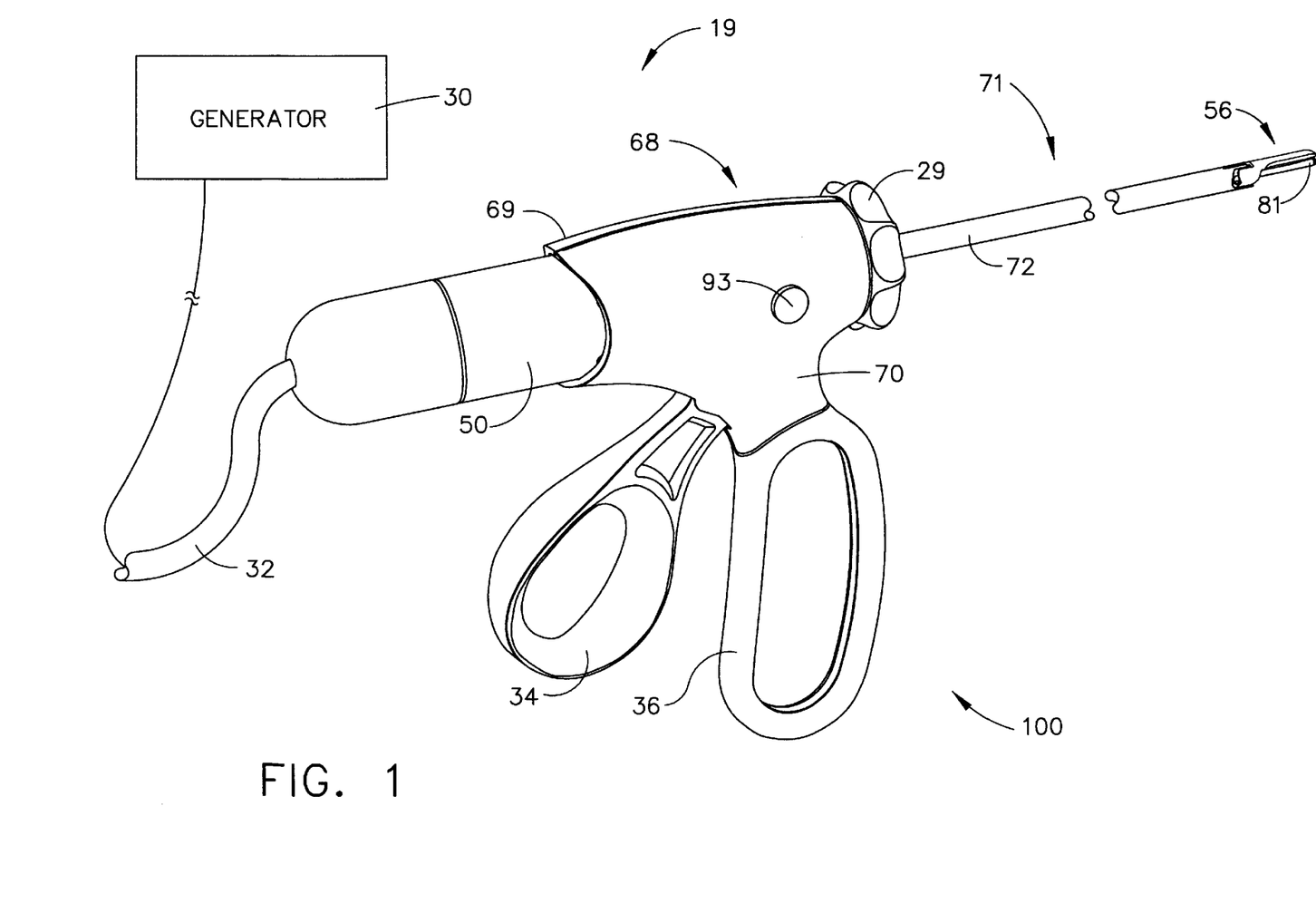
FIG. 1 is a perspective view illustrating an embodiment of an ultrasonic surgical instrument in accordance with the present invention.
Figure 3:
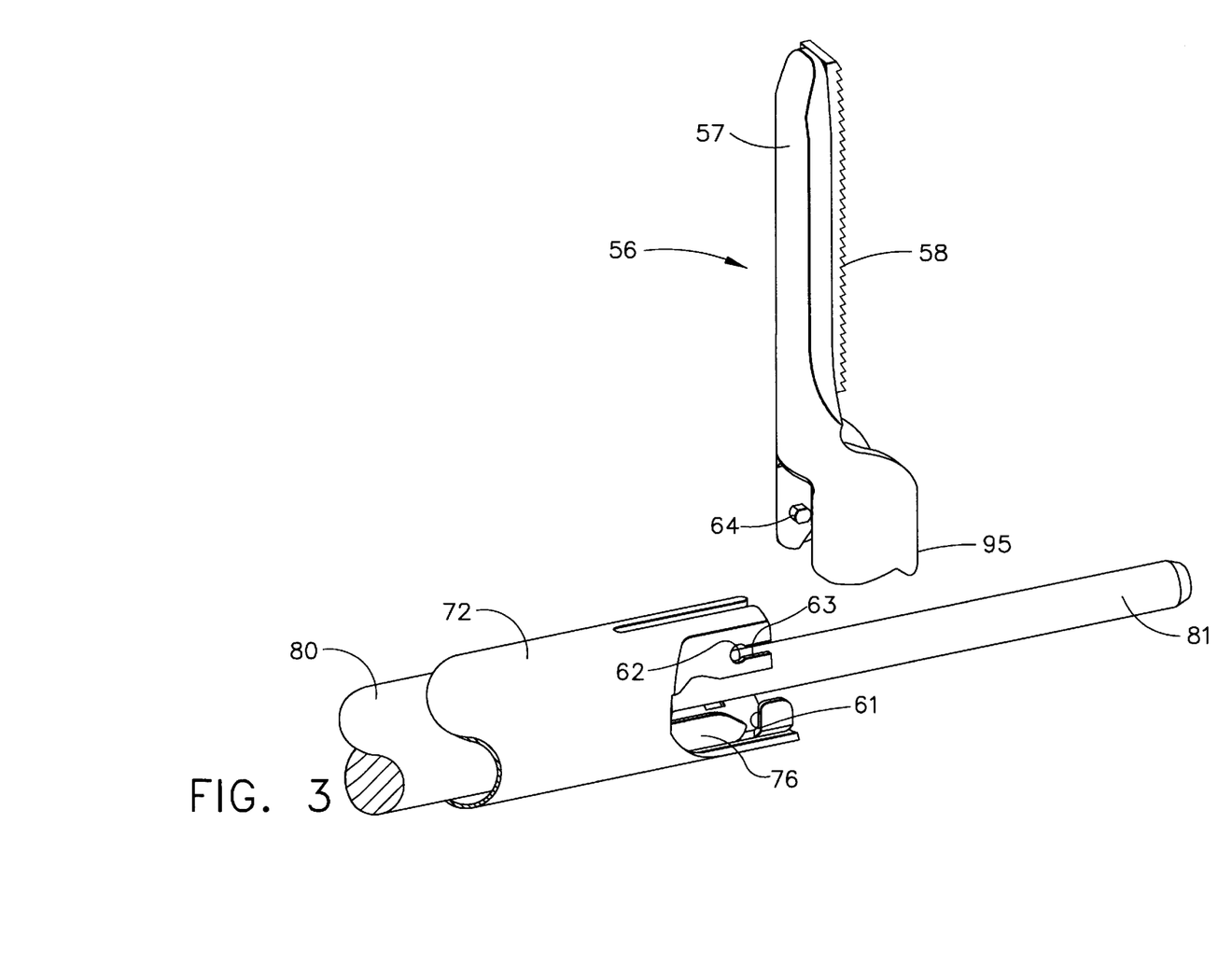
FIG. 3 is a perspective view illustrating the distal portion of an ultrasonic surgical instrument with its clamp arm removed in accordance with the present invention.

With reference first to FIGS. 1 and 3, a present embodiment of a surgical system 19, including an ultrasonic surgical instrument 100 in accordance with the present invention is illustrated. The surgical system 19 includes an ultrasonic generator 30, an ultrasonic transducer 50, and an ultrasonic surgical instrument 100. It will be noted that, in some applications, the ultrasonic transducer 50 is referred to as a "hand piece assembly" because the surgical instrument of the surgical system 19 is configured such that a surgeon grasps and manipulates the ultrasonic transducer 50 during various procedures and operations. The ultrasonic surgical instrument 100 may include a scissors-like grip arrangement which facilitates positioning and manipulation of the instrument apart from manipulation of the ultrasonic transducer 50.

Referring to FIG. 1, the ultrasonic surgical instrument 100 includes a multi-piece handle assembly 68 adapted to isolate the operator from the vibrations of the acoustic assembly. The handle assembly 68 can be shaped to be held by a user in a conventional manner, but it is contemplated that the present ultrasonic surgical instrument 100 principally be grasped and manipulated by a scissors-like arrangement provided by a handle assembly of the instrument, as will be described. While the multi-piece handle assembly 68 is illustrated, the handle assembly 68 may comprise a single or unitary component. The proximal end of the ultrasonic surgical instrument 100 receives and is fitted to the distal end of the ultrasonic transducer 50 by insertion of the transducer into the handle assembly 68. The ultrasonic surgical instrument 100 may be attached to and removed from the ultrasonic transducer 50 as a unit. A suitable ultrasonic transducer 50 is Model No. HP050, which is available from Ethicon Endo-Surgery, Inc.

The ultrasonic surgical instrument 100 may include a handle assembly 68, comprising mating housing portion 69, housing portion 70, and an transmission assembly 71. When the present instrument is configured for endoscopic use, the construction can be dimensioned such that transmission assembly 71 has an outside diameter of approximately 5.5 mm. The elongated transmission assembly 71 of the ultrasonic surgical instrument 100 extends orthogonally from the instrument handle assembly 68. The transmission assembly 71 can be selectively rotated with respect to the handle assembly 68 as further described below. The handle assembly 68 may be constructed from a durable plastic, such as polyearbonate or a liquid crystal polymer. It is also contemplated that the handle assembly 68 may alternatively be made from a variety of materials including other plastics or metals.

Figure 2:
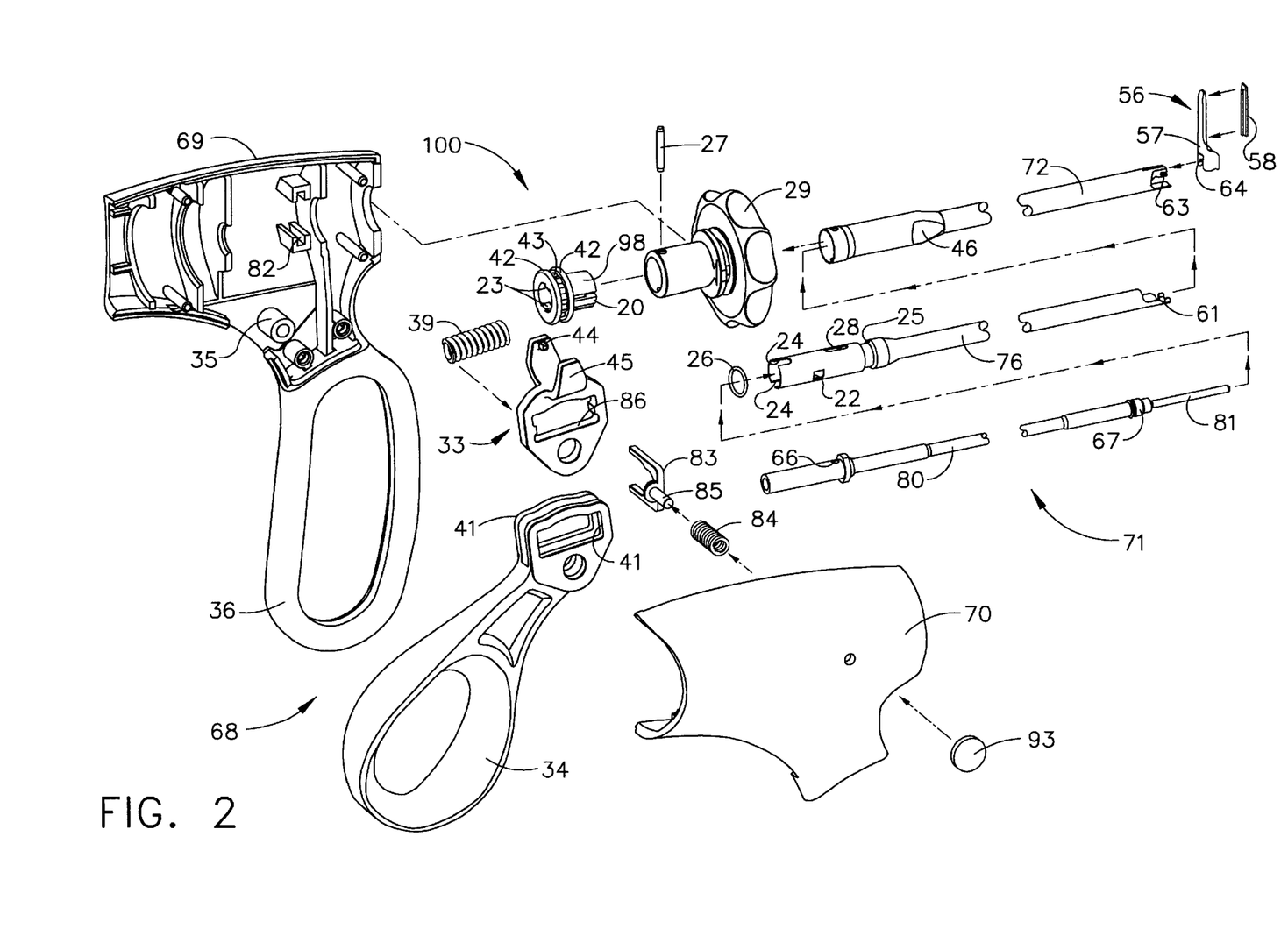
FIG. 2 is an exploded perspective view of an ultrasonic surgical instrument in accordance with the present invention.

Referring now to FIG. 2, an exploded view of the ultrasonic surgical instrument 100 of the surgical system 19 is illustrated. The transmission assembly 71 may include an outer tubular member or outer sheath 72, an inner tubular actuating member 76, a waveguide 80 and end-effector 81. As will be described, the outer sheath 72, the actuating member 76, and the waveguide 80 may be joined together for indexed rotation as a unit (together with ultrasonic transducer 50) relative to handle assembly 68.

The waveguide 80 which is adapted to transmit ultrasonic energy from transducer 50 to end-effector 81 may be flexible, semi-flexible or rigid. The waveguide 80 may also be configured to amplify the mechanical vibrations transmitted through the waveguide 80 to the end-effector 81 as is well known in the art. The waveguide 80 may further have features to control the gain of the longitudinal vibration along the waveguide 80 and features to tune the waveguide 80 to the resonant frequency of the system. In particular, waveguide 80 may have any suitable cross-sectional dimension. For example, the waveguide 80 may have a substantially uniform cross-section or the waveguide 80 may be tapered at various sections or may be tapered along its entire length.

Ultrasonic waveguide 80 may further include at least one radial hole or aperture 66 extending therethrough, substantially perpendicular to the longitudinal axis of the waveguide 80. The aperture 66, which may be positioned at a node, is configured to receive a connector pin 27 which connects the waveguide 80, to the tubular actuating member 76, and the tubular outer sheath 72, a drive collar 98, and a rotation knob 29 together for conjoint, indexed rotation relative to instrument handle assembly 68.

In one embodiment of the present invention, the ultrasonic waveguide 80 may have a plurality of grooves or notches (not shown) formed in its outer circumference. The grooves may be located at nodes of the waveguide 80 to act as alignment indicators for the installation of a damping sheath (not shown) and stabilizing silicone rings or compliant supports during manufacturing. A seal 67 may be provided at the distal-most node, nearest the end-effector 81, to abate passage of tissue, blood, and other material in the region between the waveguide 80 and actuating member 76.

The end-effector 81 of the waveguide 80 may be integral therewith and formed as a single unit. The end-effector 81 may alternately be connected by a threaded connection, a welded joint, or other coupling mechanisms. The distal end of the end-effector 81 is disposed near an anti-node in order to tune the acoustic assembly to a preferred resonant frequency $f_o$ when the acoustic assembly is not loaded by tissue. When ultrasonic transducer 50 is energized, the distal end of the end-effector 81 is configured to move longitudinally in the range of, for example, approximately 10 to 500 microns peak-to-peak, and preferably in the range of about 20 to about 200 microns at a predetermined vibrational frequency $f_o$ of, for example, 55,500 Hz.

In accordance with the illustrated embodiment shown in FIGS. 1–3, the end-effector 81, sometimes referred to as a blade, may be cylindrical for cooperation with the associated clamping mechanism of the present clamp coagulator instrument. The end-effector 81 may receive suitable surface treatment or shaping, as is known in the art.

Ultrasonic transducer 50, and an ultrasonic waveguide 80 of the ultrasonic surgical instrument 100, together provide an acoustic assembly of the present surgical system 19, with the acoustic assembly providing ultrasonic energy for surgical procedures when powered by generator 30. The acoustic assembly of surgical instrument 100 generally includes a first acoustic portion and a second acoustic portion. In the present embodiment, the first acoustic portion comprises the ultrasonically active portions of ultrasonic transducer 50, and the second acoustic portion comprises the ultrasonically active portions of transmission assembly 71. Further, in the present embodiment, the distal end of the first acoustic portion is operatively coupled to the proximal end of the second acoustic portion by, for example, a threaded connection.

Figure 6:
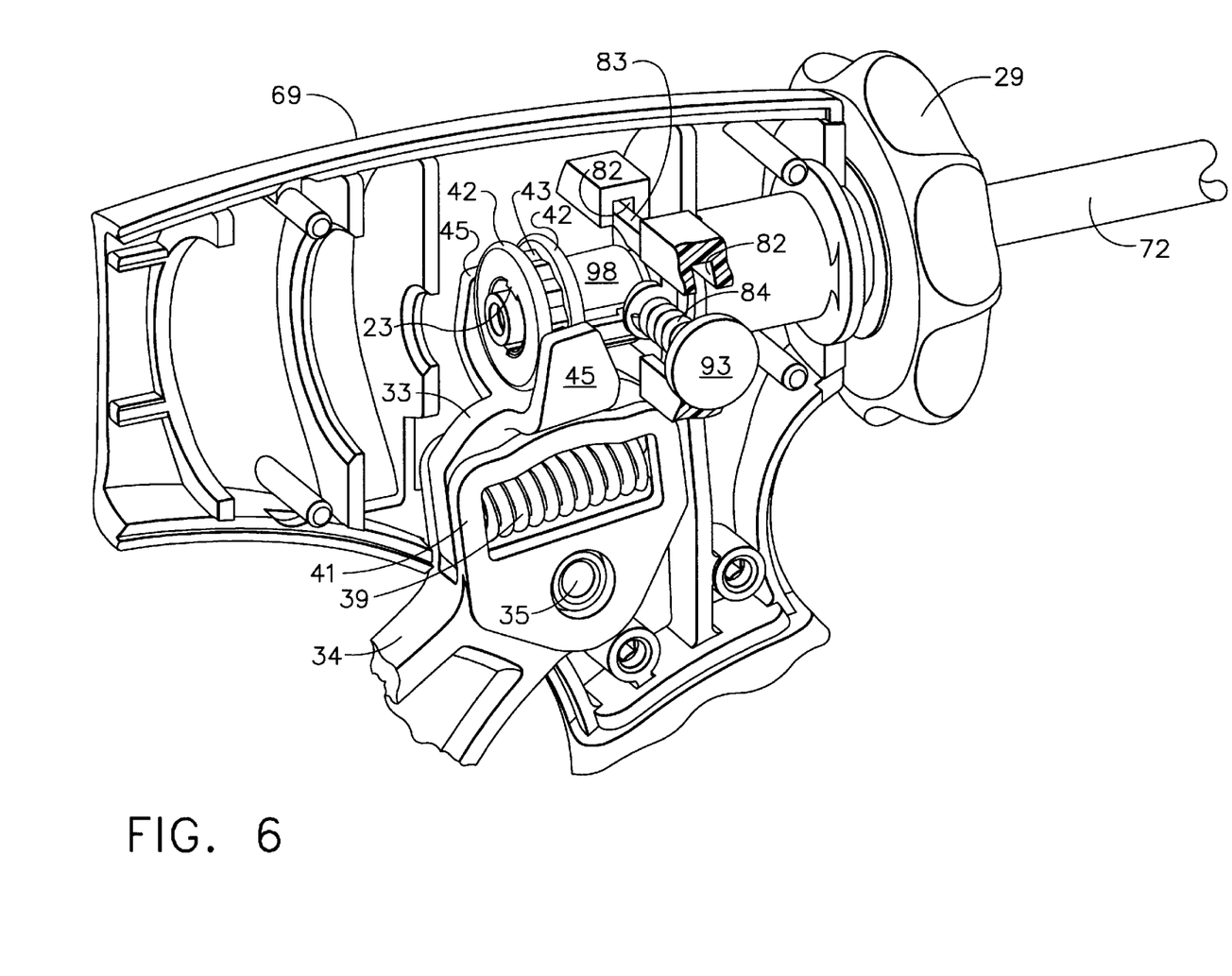
FIG. 6 is a cutaway perspective view of the proximal portion of an ultrasonic surgical instrument in accordance with the present invention illustrating a clamp arm release mechanism.

With particular reference to FIGS. 2 and 6, reciprocal movement of actuating member 76 is affected by the provision of a drive collar 98 mounted on the proximal end of the actuating member for conjoint rotation. Drive collar 98 includes a pair of diametrically opposed axially extending lugs 20 in engagement with suitable openings 22 in the proximal portion of tubular actuating member 76. Rotation of the drive collar 98 together with the actuating member 76 is further affected by the provision of a pair of keys 23 diametrically engageable with suitable key openings 24 defined by the proximal end of the actuating member 76. A circumferential groove 25 on the actuating member 76 receives on O-ring 26 for engagement with the inside surface of outer sheath 72.

Rotation of the actuating member 76 together with tubular outer sheath 72 and inner waveguide 80 is provided by a connector pin 27 extending through these components of the instrument. Tubular actuating member 76 includes an longated slot 28 through which the connector pin 27 extends to accommodate reciprocal movement of the actuating member 76 relative to the outer sheath 72 and inner waveguide 80.

The drive collar 98 provides a portion of the clamp drive mechanism of the instrument which affects pivotal movement of the clamp arm 56 by reciprocation of actuating member 76. The clamp drive mechanism further includes a drive yoke 33 which is operatively connected with an operating lever 34 of the instrument, with the operating lever thus interconnected with the reciprocable actuating member 76 via drive yoke 33 and drive collar 98. The operating lever 34 is pivotally connectable to the handle assembly 68 of the instrument, by a pivot mount 35, for cooperation in a scissors-like fashion with a handgrip 36 of the handle assembly 68. Movement of lever 34 toward handgrip 36 translates actuating member 76 proximally, thereby pivoting clamp arm 56 toward end-effector 81. The scissors-like action provided by pivotal operating lever 34 and cooperating handgrip 36 facilitates convenient and efficient manipulation and positioning of the instrument, and operation of the clamping mechanism at the distal portion of the instrument whereby tissue is efficiently urged against the end-effector 81.

Operative connection of the drive yoke 33 with the operating lever 34 is provided by a compression coil spring 39. The spring 39 fits within a spring slot 86 defined by the drive yoke 33, which in turn is positioned between a pair of spring flanges 41 of the operating lever 34. The drive yoke 33 is pivotally movable with respect to the spring flanges 41 (about pivot mount 35 of handle assembly 68) in opposition to the force exerted by compression coil spring 39, which bears against the surfaces of the spring slots 86 defined by each of the spring flanges 41. In this manner, the force which can be applied to the actuating member 76, by pivotal movement of operating lever 34 acting through drive yoke 33 and drive collar 98, is limited by the force with which spring 39 bears against the spring flanges spring flange 41. Application of excessive force results in pivotal displacement of drive yoke 33 relative to the spring flanges spring flange 41 of the operating lever 34 in opposition to spring 39.

Referring to FIGS. 2 and 6, clamp arm 56 is detachably mounted to the distal end of the support tube, outer sheath 72. Actuation member 76 is operatively coupled to the clamp arm 56. The ultrasonic surgical instrument 100 may also include a clamp arm release 93. The actuation member 76 includes a first range of motion and a second range of motion, whereby moving the clamp arm release 93 from a second position to a first position increases allowable motion of the actuation member 76 from the second range of motion to the first range of motion, thereby facilitating release of the clamp arm 56 from the outer sheath 72. Clamp arm release 93 stop 83 rides over the proximal cylindrical portion of rotation knob 29, distal to drive collar 98. Stop 83 slides within race 82, and is biased against housing 69 by spring 84. Spring 84 surrounds post 85 of stop 83. Post 85 extends through housing 70 to clamp arm release 93. Clamp arm release 93 is normally biased against housing 70, trapping drive collar 98 and limiting actuating member 76 range of travel. Clamp arm release 93 may be pulled against the action of spring 84, releasing drive collar 98 from limit by stop 83, thereby allowing motion of the actuation member 76 from the second range of motion to the first range of motion, thereby facilitating release of the clamp arm 56 from the outer sheath 72.

Indexed rotational positioning of the transmission assembly 71 of the present ultrasonic surgical instrument 100 is provided by the provision of a detent mechanism incorporated into the clamp drive mechanism of the instrument. Specifically, the drive collar 98 includes a pair of axially spaced apart drive flanges 42. A detent-receiving surface is provided between the drive flanges 42, and defines a plurality of circumferentially spaced teeth 43 which define detent-receiving depressions generally about the periphery of the drive collar 98.

Indexed rotational movement is further achieved by the provision of at least one, and preferably a pair, of diametrically opposed detents 44 respectively provided on cantilevered yoke arms 45 of drive yoke 33. By this arrangement, the yoke arms 45 are positioned between the drive flanges 42 for engagement with the confronting surfaces thereof, and bias the detents 44 into engagement with the drive collar 98. The detent mechanism resists rotation of the ultrasonic transducer, and associated cable assembly, with respect to the handle assembly 68 with the resistance to rotation readily and conveniently overcome by application of sufficient torque via rotation knob 29.

Rotation of the transmission assembly 71 of ultrasonic surgical instrument 100 may be affected together with relative rotational movement of ultrasonic transducer 50 with respect to instrument handle assembly 68. In order to join the transmission assembly 71 to the ultrasonic transducer 50 in ultrasonic-transmitting relationship, the proximal portion of the outer sheath 72 may be provided with a pair of wrench flats 46. The wrench flats 46 allow torque to be applied by a suitable torque wrench or the like to thereby permit the waveguide 80 to be joined to the ultrasonic transducer 50. The ultrasonic transducer 50, as well as the transmission assembly 71, are thus rotatable, as a unit, by suitable manipulation of rotation knob 29, relative to handle assembly 68 of the instrument. The interior of handle assembly 68 is dimensioned to accommodate such relative rotation of the ultrasonic transducer 50.

Figure 4:
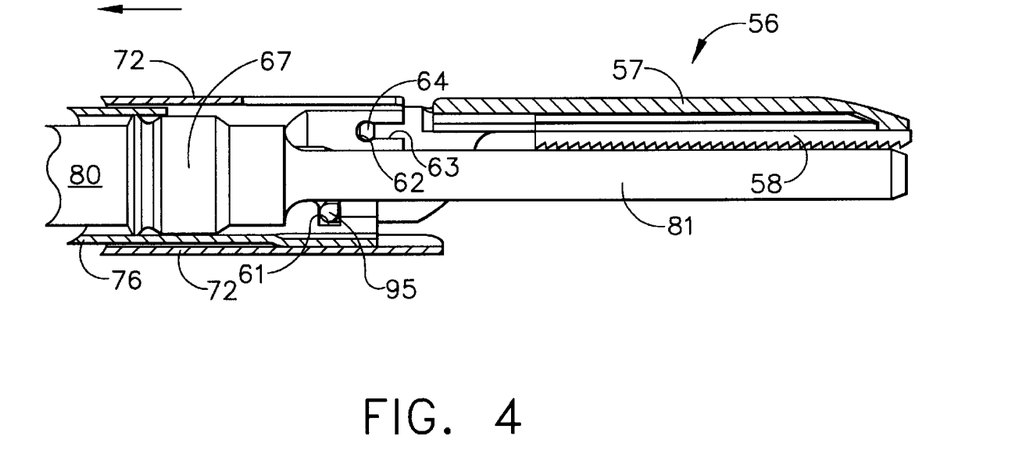
FIG. 4 is a side sectional view of the distal portion of an ultrasonic surgical instrument in accordance with the present invention with its attached clamp arm in a closed position.
Figure 5:
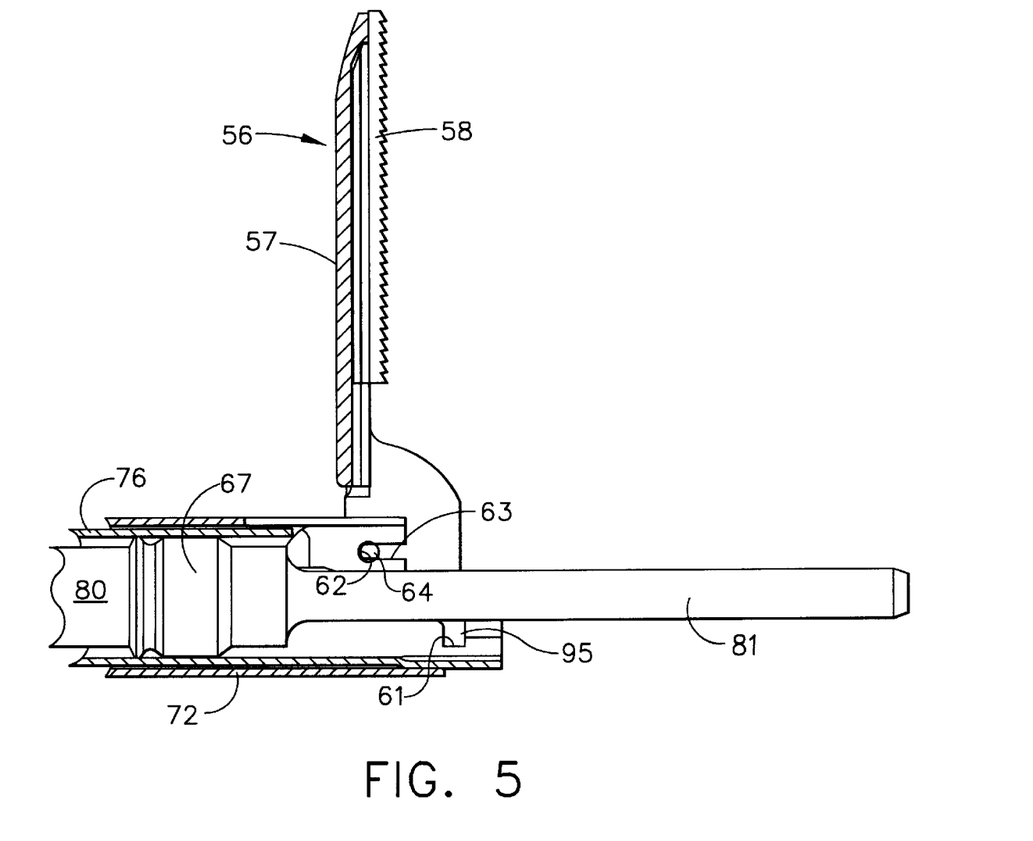
FIG. 5 is a side sectional view of the distal portion of an ultrasonic surgical instrument in accordance with the present invention with its attached clamp arm in an open and removable position.

With particular reference to FIGS. 3–5, therein is illustrated the clamping mechanism of the present ultrasonic surgical instrument 100, which is configured for cooperative action with the end-effector 81 of the waveguide 80. The clamping mechanism includes a pivotally movable clamp arm 56, which is connectable to the distal end of outer sheath 72. A clamp pad 58, preferably formed from TEFLON®, trademark name of E. I. Du Pont de Nemours and Company for a low coefficient of friction polymer material, or other suitable low-friction material, is mounted on the surface of the clamp arm 56 for cooperation with the end-effector 81, with pivotal movement of the clamp arm 56 positioning the clamp pad in substantially parallel relationship to, and in contact with, the end-effector 81. By this construction, tissue to be clamped is grasped between the clamp pad 58 and the end-effector 81. As illustrated, the clamp pad 58 may be provided with a sawtooth-like configuration to enhance the gripping of tissue in cooperation with the end-effector 81.

Pivotal movement of the clamp arm 56 with respect to the end-effector 81 is affected by the provision of at least one, and preferably a pair of levers 95 of the clamp arm 56 at the proximal end of clamp arm 56. The levers 95 are in operative engagement with a actuation slot 61 of the reciprocally actuating member 76. Reciprocal movement of the actuating member 76, relative to the outer sheath 72 and the waveguide 80, thereby affects pivotal movement of the clamp arm 56 relative to the end-effector 81. FIGS. 3–5 further illustrate an arrangement for replaceably mounting clamp arm 56 of the instrument on the associated outer sheath 72. A replaceable pivotal clamp arm 56 of the instrument includes an elongated clamp portion 57 on which a tissue-contacting clamp pad 58 is positioned.

The clamp arm 56 includes pivot pin 64, and levers 95. Levers 95 are positionable in operative engagement with the reciprocable actuating member 76 in actuating slot 61 of the present instrument. The clamp arm 56 is thus pivotal about a pivot axis defined by pivot pin 64.

In order to create the desired ultrasonic effect on tissue clamped between clamp arm 56 and the associated end-effector 81, it is desirable to have clamp arm 56 positioned in substantial alignment with the end-effector 81, that is, aligned such that the longitudinal axis of the end-effector 81 is in the same plane as a longitudinal axis extending through the clamp arm 56. At the same time, it is desired that components of the present instrument, including the clamp arm 56, be configured for disposable, single-patient use. As such, it is desirable to provide a replaceable clamp arm 56 providing for the remainder of ultrasonic surgical instrument 100 to be reusable.

The present invention is particularly configured to allow the replacement of clamp arm 56. FIGS. 4 and 5 depict how the clamp arm 56 is removed. Clamp arm 56 is moved from a first position, shown in FIG. 4, where the clamp arm 56 is parallel to end-effector 81, to a second position, shown in FIG. 5, where clamp arm 56 is perpendicular to end-effector 81. Positioning clamp arm 56 perpendicular to end-effector 81 aligns actuation slot 61 and mounting slot 63 such that clamp arm 56 can be removed from actuation slot 61 and mounting slot 63 simultaneously. Re-assembly of a new clamp arm 56 is accomplished by reversing the process and sliding pivot pin 64 into mounting slot 63 as levers 95 are slid into actuation slot 61. It will be noted that pivot pin 64 is particularly adapted to slide into slot 61 with clamp arm 56 in its fully open position. In particular, pivot pin 64 has a cross sectional area which is longer along a first axis than along a second axis which is perpendicular to the first axis. Further, the sides of pivot pin 64 which are parallel to the longer first axis of pivot pin 64 are flattened and the width along the second axis is smaller than the width of slot 61 to facilitate movement through slot 61. The second and third sides of pivot pin 64 are rounded to prevent pivot pin 64 from moving through slot 61 with clamp arm 56 in its operative mode, for example, as illustrated in FIG. 4. To facilitate the engagement of pivot pin 64, slot 61 includes a rounded hole 62 at its proximal end. Rounded hole 62 is adapted to hold clamp arm 56 in place when clamp arm 56 is in its operative position, for example, as illustrated in FIG. 4. Rounded hole 62 is larger in diameter than slot 61 and the first cross sectional axis of pivot pin 64.

Actuation member 76 is operatively coupled to the clamp arm 56 and limited to a second range of motion when stop 83 traps drive collar 98. Stop 83 prevents actuation slot 61 from disengaging with levers 95. When stop 83 is released by pulling clamp arm release 93, a first range of motion of actuation member 76 is allowed, thereby facilitating release of the clamp arm 56 from the outer sheath 72 by disengaging levers 95 from actuation slot 61 as pivot pin 64 is removed from rounded hole 62 through mounting slot 63. Clamp arm release 93 may be pulled against the action of spring 84, releasing drive collar 98 from limit by stop 83, thereby allowing motion of the actuation member 76 from the second range of motion to the first range of motion, thereby facilitating release of the clamp arm 56 from the outer sheath 72.

Figure 7:
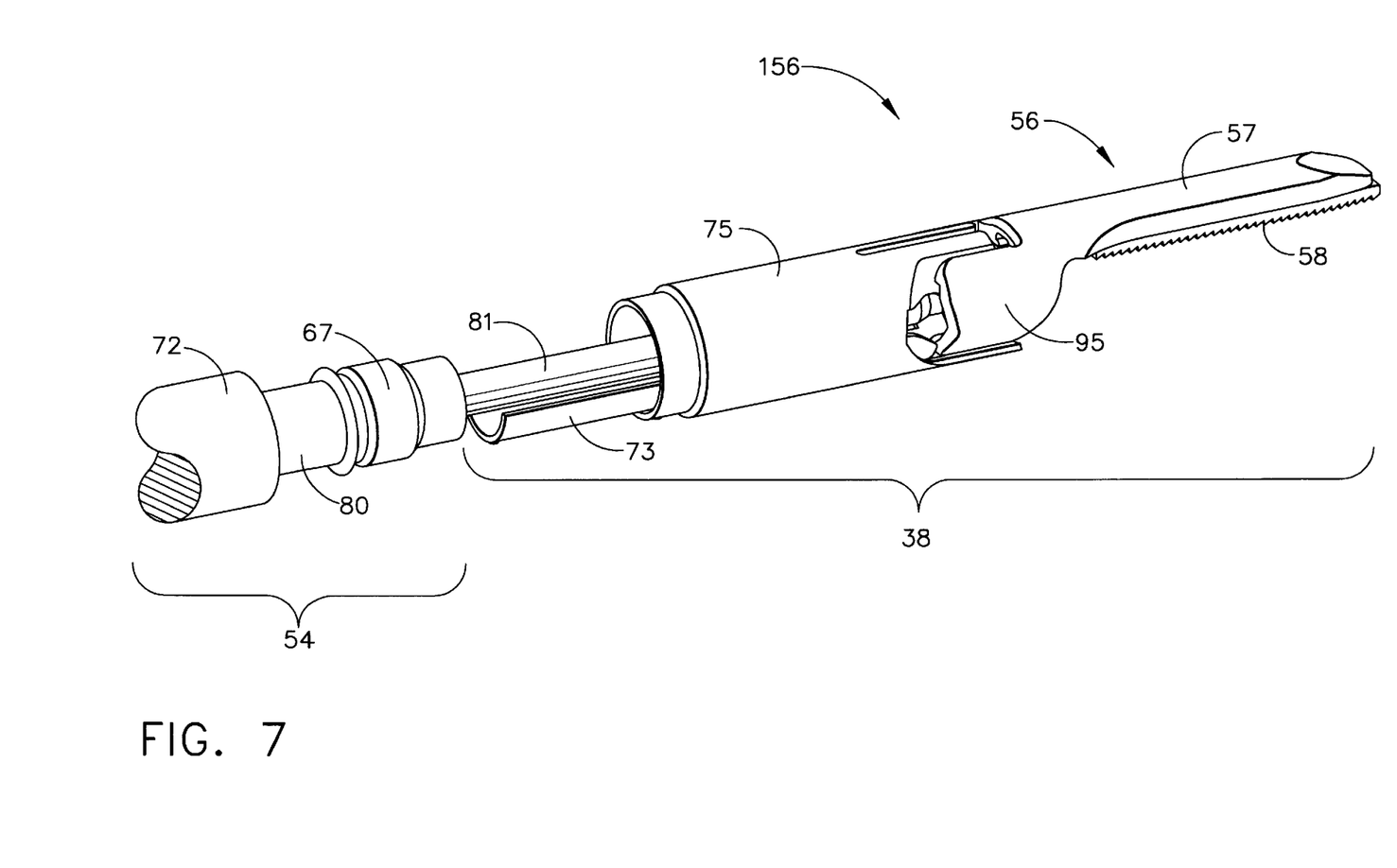
FIG. 7 is a perspective view of an alternate embodiment of a removable clamp arm in accordance with the present invention.
Figure 8:
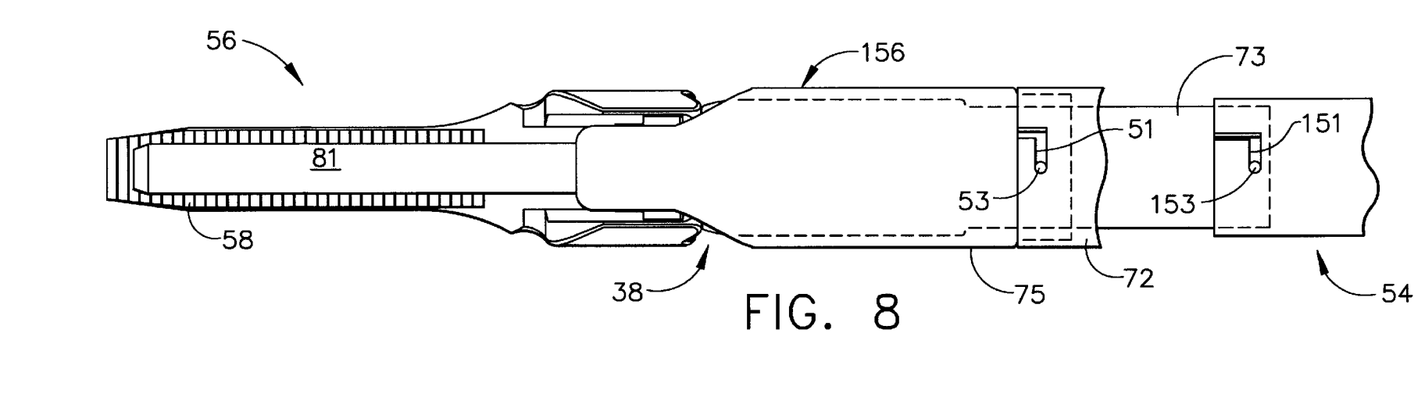
FIG. 8 is a bottom view of the clamp arm assembly illustrated in FIG. 7.
Figure 9:
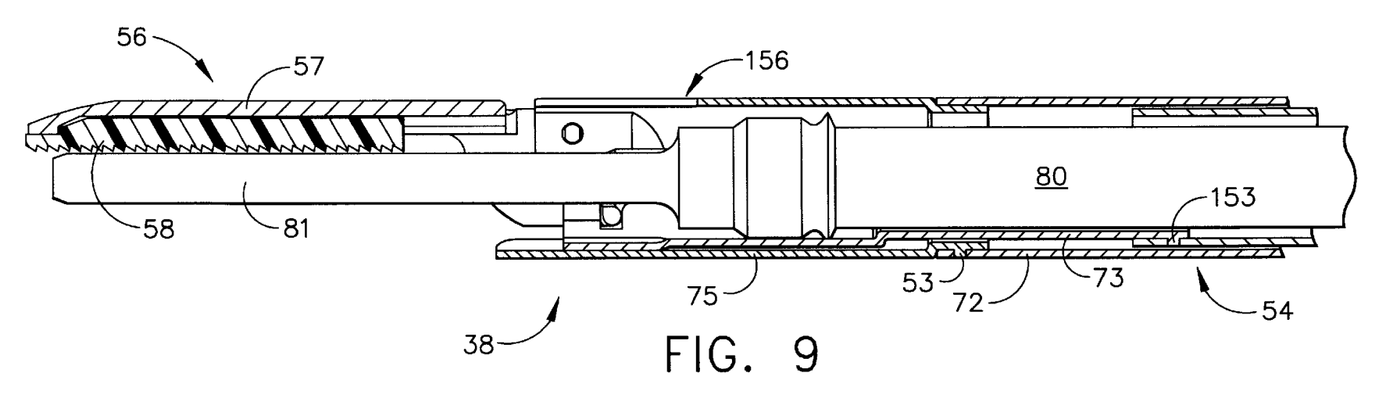
FIG. 9 is a side sectional view of the clamp arm assembly illustrated in FIG. 7.

FIGS. 7–9 illustrate a second embodiment of a replaceable clamp arm 56 mount according to the present invention. Like the previous embodiment, the clamp arm mount 156 is provided at the distal end of outer sheath 72. This embodiment utilizes a bayonet type mount where outer sheath 72 is separable into a reuseable portion 54, and a disposable portion 38. Clamp arm 56 is fixed to disposable portion 38 with pivot pin 64.

In the embodiment illustrated in FIGS. 7–9, the distal portion of outer sheath 72 includes at least one L-shaped slot 51 while the distal portion of actuating member 76 includes at least one L-shaped slot 151. The portion of outer sheath 72 on disposable portion 38, which may be referred to as outer-tube disposable 75, includes at least one attachment pin 53 insertable into L-shaped slot 51. The portion of actuating member 76 on disposable portion 38, which may be referred to as inner-tube disposable 73, includes at least one attachment pin 153 insertable into L-shaped slot 151. Disposable portion 38 includes clamp arm 56 attached to outer-tube disposable 75, and inner-tube disposable 73. In this embodiment, disposable portion 38 is held in place by attachment pin 53 and attachment pin 153. In the illustrated embodiment, L-shaped slot 51 of outer sheath 72 is adapted to receive attachment pin 53 while L-shaped slot 151 of actuating member 76 is adapted to receive attachment pin 153. Thus, outer sheath 72 is attached to outer-tube disposable 75 by sliding outer tube attachment pin 53 into L-shaped slot 51 while actuating member 76 is attached to inner-tube disposable 73 by sliding inner tube attachment pin 153 into L-shaped slot 151.

It is sometimes desirable to replace end-effector 81 along with disposable portion 38. This may be accomplished by including end-effector 81 into disposable portion 38. In such an instrument, coupling of waveguide 80 to disposable portion 77 may be accomplished by acoustically coupling through a node to node connection.

Figure 10:
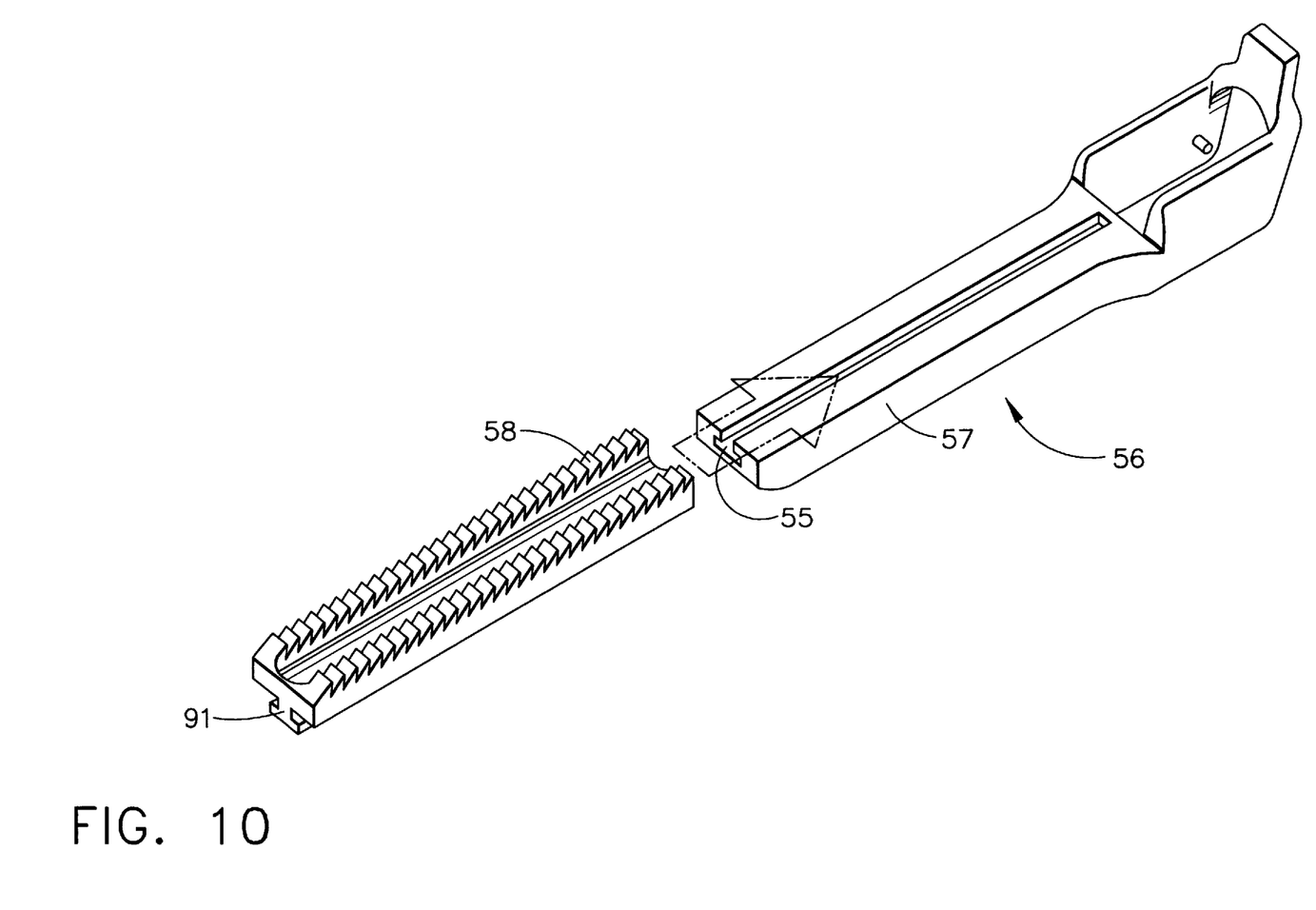
FIG. 10 is a perspective view of a clamp arm in accordance with the present invention with an exchangeable clamp pad feature.
Figure 11:
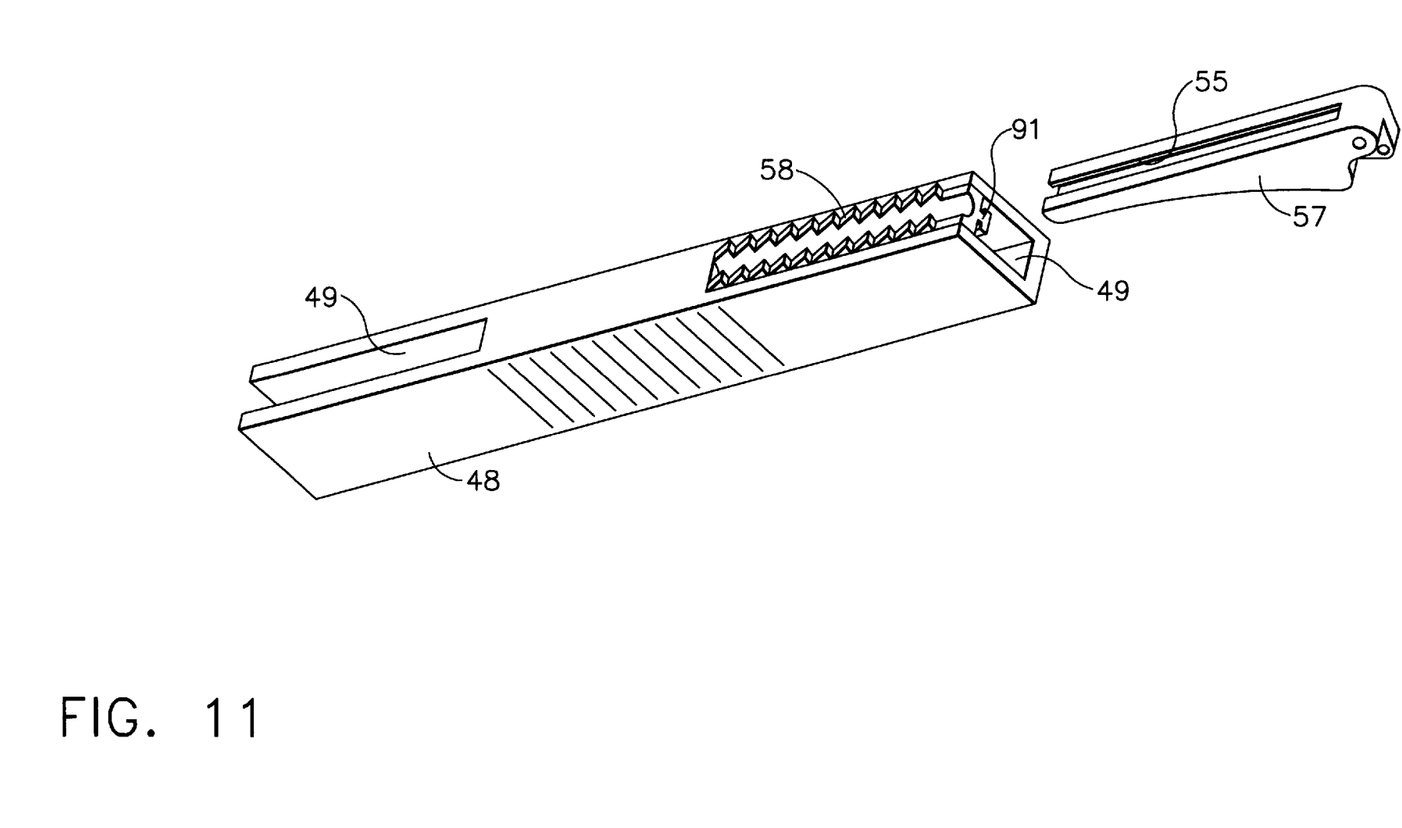
FIG. 11 is a perspective view of a cartridge for removing and loading clamp pads from a clamp arm in accordance with the present invention.

FIGS. 10 and 11 illustrate a method of a replacing clamp pad 58. Clamp pad 58 is inserted into and removed from clamp portion 57 utilizing a T-shaped slot 55 within clamp portion 57 which accepts a clamp pad having a T-shaped flange 91. It is contemplated that T-shaped pad 91 is fabricated from a polymeric material such as TEFLON, and that clamp portion 57 is fabricated from metal, such as stainless steel, or titanium. Clamp portion 57, being formed from metal, would have a useful life of many procedures, whereas clamp pad 58, being formed from a polymer, may need to be replaced several times, for example, during a long surgical procedure. Replacement of clamp pad 58 during a surgical procedure may be facilitated by insertion instrument 48, which is shown in FIG. 11. Insertion instrument 48 may include one or more sterile clamp pads 58, and clamp pad receptacles 49.

Replacement of clamp pad 58 would include the steps of; 1) sliding clamp portion 57 into receptacle 49, disengaging old clamp pad 58 from its slot T-shaped slot 55; 2) removing clamp portion 57 from insertion instrument 48 leaving old clamp pad 58 within receptacle 49. 3) inserting clamp portion 57 into insertion instrument 48, sliding new clamp pad 58 into T-shaped slot 55, attaching new clamp pad 58 to clamp portion 57; and 4) removing clamp portion 57 from insertion instrument 48.

While embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An ultrasonic surgical instrument comprising:
   A) a transducer, wherein said transducer is adapted to convert electrical energy into mechanical motion;
   B) an ultrasonic surgical instrument comprising:
      i) a handle assembly, wherein said handle assembly is adapted to receive said transducer;
      ii) a waveguide extending distally from said handle assembly, wherein said waveguide is adapted to be acoustically coupled to said transducer, and wherein said waveguide is adapted to transmit ultrasonic energy therethrough;
      iii) an end-effector located at a distal end of said waveguide;
      iv) a support tube extending from said handle assembly and surrounding at least a portion of said waveguide, said support tube terminating proximal to at least a portion of said end-effector;
      v) a clamp arm mounted to the distal end of said support tube, wherein said clamp arm is detachably mounted to said support tube; and
      vi) an actuation element comprising a clamp arm release, said clamp arm release comprising an actuation limiting element, wherein said actuation element operatively couples said handle assembly to said clamp arm, said actuation element including slots adapted to receive a proximal portion of said clamp arm, wherein said actuation limiting element limits movement of said actuation element.

2. An ultrasonic surgical instrument according to claim 1, wherein said proximal portion of said clamp arm includes first and second pivot pins adapted to slide into said slots.

3. An ultrasonic surgical instrument according to claim 2 wherein said first and second pivot pins have an asymmetric cross section with a first cross sectional axis which is longer than a second cross sectional axis, said first cross sectional axis being longer than said second cross sectional axis.

4. An ultrasonic surgical instrument according to claim 3 wherein said first and second pivot pins have first and second sides, said first and second sides being substantially flat and substantially parallel to said first cross sectional axis.

5. An ultrasonic surgical instrument according to claim 4 wherein said first and second pivot pins have third and fourth sides which are positioned generally perpendicular to said first and second sides, said third and fourth sides being rounded.

6. An ultrasonic surgical instrument according to claim 5 wherein said slots have a width and include a rounded hole at a proximal end thereof, said rounded hole having a diameter greater than said slot width.

7. An ultrasonic surgical instrument according to claim 6 wherein said slot width is less than said first cross sectional axis and greater than said second cross sectional axis and said diameter of said rounded hole is greater than said first cross sectional axis.

8. An ultrasonic surgical instrument according to claim 1, wherein said handle assembly includes said clamp arm release operatively connected to said clamp arm, wherein movement of said clamp arm release to a first position facilitates removal of said clamp arm from said support tube.

9. An ultrasonic surgical instrument according to claim 8, wherein said actuation element comprises a first range of motion and a second range of motion, whereby moving said clamp arm release from a second position to said first position increases allowable motion of said actuation element from said second range of motion to said first range of motion, thereby facilitating release of said clamp arm from said support tube.

10. An ultrasonic surgical instrument comprising:
    A) a handle assembly;
    B) a waveguide partially in said handle assembly and extending distally from said handle assembly, wherein said waveguide is adapted to transmit ultrasonic energy therethrough;
    C) an end-effector located at the distal end of said waveguide;
    D) a support tube extending from said handle assembly and surrounding at least a portion of said waveguide, said support tube terminating proximal to said end-effector;
    E) a clamp arm mounted to the distal end of said support tube, wherein said clamp arm is detachably mounted to said support tube; and F) an actuation element comprising a clamp arm release, said clamp arm release comprising an actuation limiting element, wherein said actuation element is operatively coupled to said clamp arm, wherein said actuation limiting element limits movement of said actuation element.

11. An ultrasonic surgical instrument according to claim 10, wherein said actuation element comprises an actuation tube extending from said handle assembly and surrounding at least a portion of said waveguide, said actuation tube terminating proximal to said end-effector, wherein said actuation tube includes slots adapted to receive a proximal portion of said clamp arm.

12. An ultrasonic surgical instrument according to claim 11, wherein said handle assembly includes a clamp arm release operatively connected to said clamp arm, wherein movement of said clamp arm release to a first position facilitates removal of said clamp arm from said support tube.

13. An ultrasonic surgical instrument according to claim 12, wherein said actuation element comprises a first range of motion and a second range of motion, whereby moving said clamp arm release from a second position to said first position increases allowable motion of said actuation element from said second range of motion to said first range of motion, thereby facilitating release of said clamp arm from said support tube.

14. An ultrasonic surgical instrument comprising:
A) a handle assembly;
B) a waveguide partially in said handle assembly and extending distally from said handle assembly, wherein said waveguide is adapted to transmit ultrasonic energy therethrough;
C) an end-effector located at the distal end of said waveguide;
D) a support tube extending from said handle assembly and surrounding at least a portion of said waveguide, said support tube terminating proximal to said end-effector, wherein said support tube is separable into at least two portions;
E) a clamp arm mounted to a distal portion of said separable support tube; and
F) an actuation element comprising a clamp arm release, said clamp arm release comprising an actuation limiting element, wherein said actuation element is separable into at least two portions and wherein said actuation element is operatively coupled to said clamp arm, wherein said actuation limiting element limits movement of said actuation element.

15. An ultrasonic surgical instrument according to claim 14, wherein said actuation element comprises an actuation tube comprising a proximal portion and a distal portion, said proximal portion of said actuation tube extending from said handle assembly to the proximal end of said distal portion of said actuation element and surrounding said waveguide, said distal portion of said actuation tube terminating proximal to said end-effector, wherein said actuation tube is operatively coupled to a proximal portion of said clamp arm.

16. An ultrasonic surgical instrument according to claim 14, wherein said clamp arm, actuation element, support tube and waveguide are adapted to rotate within said handle assembly.

17. An ultrasonic surgical instrument according to claim 15, wherein said clamp arm, actuation element, support tube and waveguide are adapted to rotate within said handle assembly.

18. An ultrasonic surgical instrument according to claim 17, wherein said proximal end of said distal portion of said actuation tube comprises a pin extending from said actuation tube, and the distal end of said proximal portion of said actuation tube comprises a slot adapted to receive said pin.

19. An ultrasonic surgical instrument comprising:
i) a handle assembly;
ii) a waveguide partially in said handle assembly and extending distally from said handle assembly, wherein said waveguide is adapted to transmit ultrasonic energy therethrough;
iii) an end-effector located at the distal end of said waveguide;
iv) a support tube extending from said handle assembly and surrounding at least a portion of said waveguide, said support tube terminating proximal to said end-effector;
v) a clamp arm mounted to the distal end of said support tube, wherein said clamp arm is detachably mounted to said support tube;
vi) an actuation element, wherein said actuation element is operatively coupled to said clamp arm; and
vii) a clamp arm release means for releasing said clamp arm from said support tube, wherein said clamp arm release means limits movement of said actuation element.

20. An ultrasonic surgical instrument comprising:
A) a transducer, wherein said transducer is adapted to convert electrical energy into mechanical motion;
B) an ultrasonic surgical instrument comprising:
i) a handle assembly, wherein said handle assembly is adapted to receive said transducer;
ii) a waveguide extending distally from said handle assembly, wherein said waveguide is adapted to be acoustically coupled to said transducer, and wherein said waveguide is adapted to transmit ultrasonic energy therethrough;
iii) an end-effector located at a distal end of said waveguide;
iv) a support tube extending from said handle assembly and surrounding at least a portion of said waveguide, said support tube terminating proximal to at least a portion of said end-effector;
v) a clamp arm mounted to the distal end of said support tube, wherein said clamp arm is detachably mounted to said support tube; and
vi) an actuation element comprising a clamp arm release, wherein said actuation element operatively couples said handle assembly to said clamp arm, wherein said actuation element comprises a first range of motion and a second range of motion, whereby moving said clamp arm release from a second position to a first position increases allowable motion of said actuation element from said second range of motion to said first range of motion, thereby facilitating release of said clamp arm from said support tube.

21. An ultrasonic surgical instrument comprising:
A) a handle assembly;
B) a waveguide partially in said handle assembly and extending distally from said handle assembly, wherein said waveguide is adapted to transmit ultrasonic energy therethrough;
C) an end-effector located at the distal end of said waveguide;
D) a support tube extending from said handle assembly and surrounding at least a portion of said waveguide, said support tube terminating proximal to said end-effector;
E) a clamp arm mounted to the distal end of said support tube, wherein said clamp arm is detachably mounted to said support tube; and
F) an actuation element comprising a clamp arm release, wherein said actuation element is operatively coupled to said clamp arm, wherein said actuation element comprises a first range of motion and a second range of motion, whereby moving said clamp arm release from a second position to a first position alters allowable motion of said actuation element from said second range of motion to said first range of motion, thereby facilitating release of said clamp arm from said support tube.

* * * * *